(12) United States Patent
Osman

(10) Patent No.: US 8,002,810 B2
(45) Date of Patent: *Aug. 23, 2011

(54) METHOD FOR POSTOPERATIVELY COMPRESSING A BONE GRAFT

(75) Inventor: Said G. Osman, Frederick, MD (US)

(73) Assignee: Zimmer Spine, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/632,687

(22) Filed: Dec. 7, 2009

(65) Prior Publication Data
US 2010/0137909 A1    Jun. 3, 2010

Related U.S. Application Data

(60) Continuation of application No. 11/165,056, filed on Jun. 24, 2005, now Pat. No. 7,645,295, which is a division of application No. 10/038,682, filed on Jan. 8, 2002, now Pat. No. 6,932,820.

(51) Int. Cl.
*A61B 17/66* (2006.01)
(52) U.S. Cl. ........................ 606/282; 606/252
(58) Field of Classification Search .......... 606/71, 606/282, 246, 257, 281; 74/130, 164
See application file for complete search history.

(56) References Cited

U.S. PATENT DOCUMENTS

| | | | |
|---|---|---|---|
| 2,507,681 A * | 5/1950 | Sage | ................................ 74/157 |
| 3,385,299 A | 5/1968 | Le Roy | |
| 3,604,414 A * | 9/1971 | Borges | ........................... 606/105 |
| 3,659,595 A | 5/1972 | Haboush | |
| 4,175,880 A | 11/1979 | Muller | |
| 5,129,903 A | 7/1992 | Luhr et al. | |
| 5,364,396 A | 11/1994 | Robinson et al. | |
| 5,470,333 A | 11/1995 | Ray | |
| 5,484,439 A | 1/1996 | Olson et al. | |
| 5,601,553 A | 2/1997 | Trebing et al. | |
| 5,616,142 A * | 4/1997 | Yuan et al. | ....................... 606/71 |
| 5,622,177 A | 4/1997 | Breimesser et al. | |
| 5,672,177 A * | 9/1997 | Seldin | ............................. 606/71 |
| 5,735,853 A | 4/1998 | Olerud | |

(Continued)

FOREIGN PATENT DOCUMENTS
DE         40 07 306 C1      5/1991
(Continued)

OTHER PUBLICATIONS

Sonntag, et al., "Atlantis Anterior Cervical Plate System Surgical Technique" brochure, Medtronic Sofamor Danek, US, 2000, 38 pgs.

(Continued)

*Primary Examiner* — Eduardo C Robert
*Assistant Examiner* — David W Bates
(74) *Attorney, Agent, or Firm* — Sprinkle IP Law Group

(57) ABSTRACT

A method for postoperatively compressing a bone graft between adjacent spinal vertebrae utilizing first and second plates having openings at remote ends for receiving bone screws to fix the plates to respective vertebrae on opposite sides of a bone graft-receiving site. The first and second plates have male and female parts having interlocking elements cooperable with one another enabling movement of the plates and the adjacent vertebrae to one another to progressively compress the bone graft between the adjacent vertebrae and prevent movement of the first and second plates and adjacent vertebrae away from one another.

15 Claims, 4 Drawing Sheets

U.S. PATENT DOCUMENTS

| | | | |
|---|---|---|---|
| 5,827,286 A * | 10/1998 | Incavo et al. | 606/71 |
| 5,842,822 A | 12/1998 | Everett et al. | |
| 5,876,402 A | 3/1999 | Errico et al. | |
| 5,964,762 A | 10/1999 | Biedermann et al. | |
| 6,051,007 A | 4/2000 | Hogendijk et al. | |
| 6,176,881 B1 | 1/2001 | Schar et al. | |
| 6,235,033 B1 | 5/2001 | Brace et al. | |
| 6,238,396 B1 | 5/2001 | Lombardo | |
| 6,306,136 B1 | 10/2001 | Raccelli | |
| 6,328,738 B1 * | 12/2001 | Suddaby | 606/57 |
| 6,331,179 B1 | 12/2001 | Freid et al. | |
| 6,402,756 B1 | 6/2002 | Ralph et al. | |
| 6,454,679 B1 | 9/2002 | Radow | |
| 6,454,769 B2 | 9/2002 | Wagner et al. | |
| 6,689,134 B2 | 2/2004 | Ralph et al. | |
| 6,852,113 B2 * | 2/2005 | Nathanson et al. | 606/71 |
| 6,932,820 B2 * | 8/2005 | Osman | 606/71 |
| 7,008,427 B2 | 3/2006 | Sevrain | |
| 7,044,952 B2 | 5/2006 | Michelson | |
| 7,097,645 B2 | 8/2006 | Michelson | |
| 7,118,573 B2 | 10/2006 | Michelson | |
| 7,645,295 B2 | 1/2010 | Osman | |
| 2002/0055741 A1 | 5/2002 | Schlapfer et al. | |
| 2002/0183755 A1 | 12/2002 | Michelson | |
| 2002/0183756 A1 | 12/2002 | Michelson | |
| 2002/0183757 A1 | 12/2002 | Michelson | |
| 2002/0188296 A1 | 12/2002 | Michelson | |
| 2003/0114856 A1 | 6/2003 | Nathanson et al. | |
| 2003/0130661 A1 | 7/2003 | Osman | |
| 2003/0199876 A1 | 10/2003 | Brace et al. | |
| 2003/0212399 A1 | 11/2003 | Dinh | |
| 2004/0019353 A1 | 1/2004 | Freid et al. | |
| 2004/0092939 A1 | 5/2004 | Freid et al. | |
| 2006/0200134 A1 | 9/2006 | Freid et al. | |
| 2008/0065070 A1 | 3/2008 | Freid et al. | |

FOREIGN PATENT DOCUMENTS

| | | |
|---|---|---|
| EP | 1 478 287 A2 | 11/2004 |
| FR | 2 751203 A1 | 1/1998 |
| WO | WO 01/026566 A1 | 4/2001 |
| WO | WO 01/89428 A2 | 11/2001 |
| WO | WO 03/063714 A2 | 8/2003 |
| WO | WO 03/071966 | 9/2003 |
| WO | WO 2007/035441 | 9/2007 |

OTHER PUBLICATIONS

International Search Report from the International Searching Authority mailed Jul. 17, 2003, Application No. PCT/US2003/03159, 2 pgs.
U.S. Patent and Trademark Office, Office Action issued in U.S. Appl. No. 10/038,682 mailed May 20, 2004, 7 pgs.
U.S. Patent and Trademark Office, Office Action issued in U.S. Appl. No. 10/351,283 mailed Nov. 2, 2004, 5 pgs.
U.S. Patent and Trademark Office, Office Action issued in U.S. Appl. No. 10/038,682 mailed Dec. 7, 2004, 7 pgs.
U.S. Patent and Trademark Office, Office Action issued in U.S. Appl. No. 10/351,283 mailed Apr. 13, 2005, 5 pgs.
U.S. Patent and Trademark Office, Office Action issued in U.S. Appl. No. 10/351,283 mailed Jul. 12, 2005, 5 pgs.
U.S. Patent and Trademark Office, Office Action issued in U.S. Appl. No. 10/351,283 mailed Mar. 13, 2006, 7 pgs.
U.S. Patent and Trademark Office, Office Action issued in U.S. Appl. No. 10/351,288 mailed May 16, 2006, 6 pgs.
U.S. Patent and Trademark Office, Office Action issued in U.S. Appl. No. 10/351,283 mailed Nov. 8, 2006, 5 pgs.
International Search Report and Written Opinion from the International Searching Authority mailed Jan. 2, 2007, Application No. PCT/US2006/035921, 6 pgs.
U.S. Patent and Trademark Office, Office Action issued in U.S. Appl. No. 10/351,288 mailed Feb. 12, 2007, 8 pgs.
U.S. Patent and Trademark Office, Office Action issued in U.S. Appl. No. 10/351,283 mailed May 29, 2007, 6 pgs.
Australian Government IP, Examination Report dated Nov. 2, 2007, Application No. AU2003208956, 2 pgs.
U.S. Patent and Trademark Office, Office Action issued in U.S. Appl. No. 10/351,283 mailed Nov. 19, 2007, 6 pgs.
International Preliminary Report on Patentability, Chapter I, Application No. PCT/US06/035921, mailed Apr. 3, 2008, 9 pgs.
Australian Government IP, Examination Report dated Jun. 5, 2008, Application No. AU2003208956, 2 pgs.
U.S. Patent and Trademark Office, Office Action issued in U.S. Appl. No. 11/165,056 mailed Feb. 2, 2009, 6 pgs.
Japanese Patent Office, Examination Report mailed Feb. 10, 2009, Application No. JP2003-563412, (with English translation), 5 pgs.
International Preliminary Examination Report, International Preliminary Examining Authority mailed Jul. 1, 2004, Application No. PCT/US2003/03159, 4 pgs.
U.S. Patent and Trademark Office, Office Action issued in U.S. Application No. 11/230,011 mailed Jun. 24, 2009, 6 pgs.
Written Opinion from the International Preliminary Examining Authority mailed Oct. 27, 2003, Application No. PCT/US2003/03159, 4 pgs.
Supplementary European Search Report, Application No. EP 03 70 7681, mailed Jul. 14, 2009, 5 pgs.
Office Action issued in U.S. Appl. No. 11/230,011 mailed Dec. 28, 2009, 6 pgs.
Office Action issued in U.S. Appl. No. 11/230,011 mailed Oct. 27, 2010, 9 pages.
Office Action issued in U.S. Appl. No. 11/738,319 mailed Nov. 3, 2010, 9 pages.
Office Action issued in U.S. Appl. No. 11/738,319, mailed Apr. 11, 2011, 10 pages.
Office Action issued in U.S. Appl. No. 11/230,011, mailed Apr. 27, 2011, 9 pages.

* cited by examiner

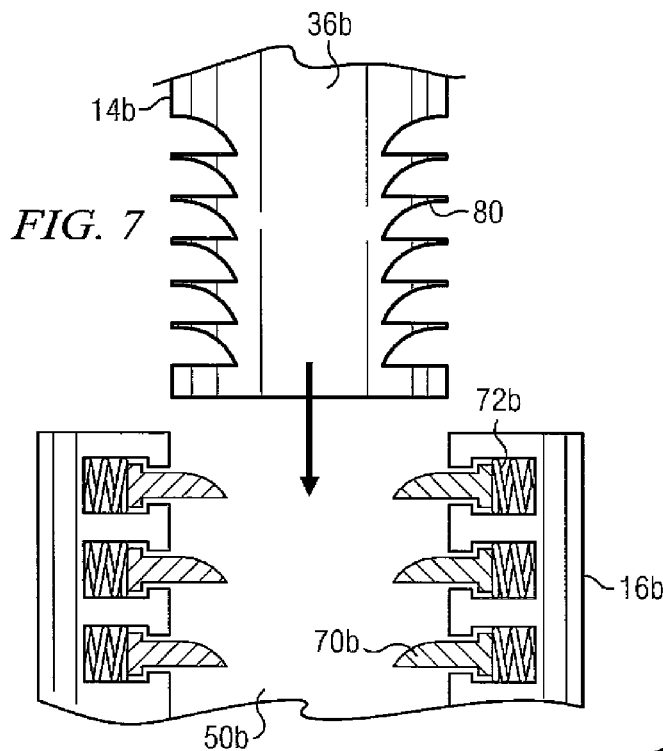
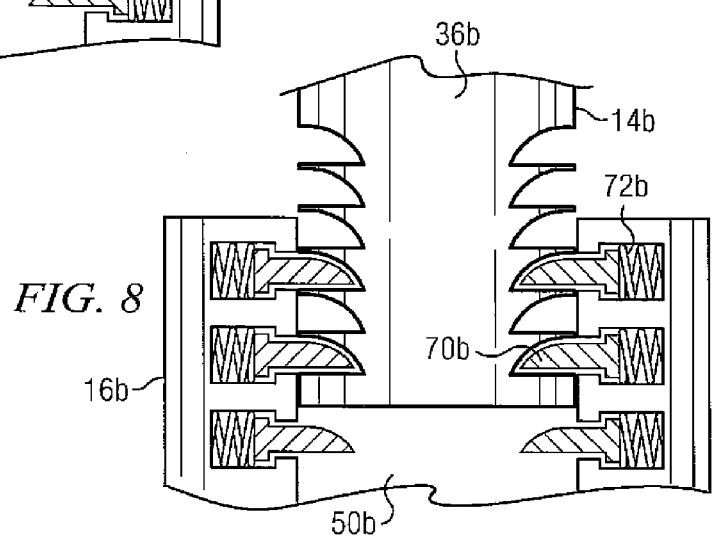
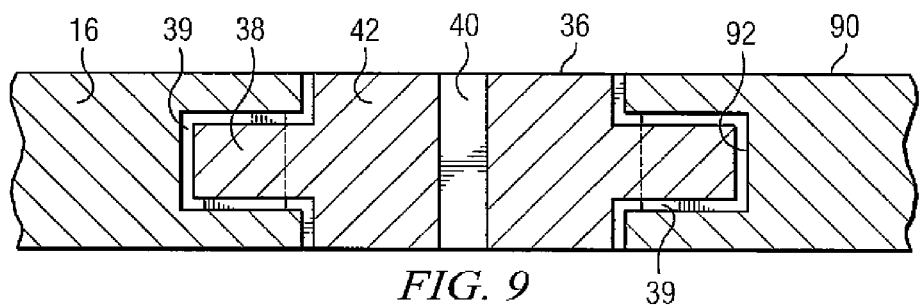

METHOD FOR POSTOPERATIVELY COMPRESSING A BONE GRAFT

CROSS-REFERENCE TO RELATED APPLICATION(S)

This is a continuation of, and claims a benefit of priority under 35 U.S.C. 120 of the filing date of U.S. patent application Ser. No. 11/165,056, filed Jun. 24, 2005, now U.S. Pat. No. 7,645,295, entitled "METHOD FOR POSTOPERATIVELY COMPRESSING A BONE GRAFT," which is a divisional of U.S. patent application Ser. No. 10/038,682, filed Jan. 8, 2002, issued as U.S. Pat. No. 6,932,820, entitled "UNI-DIRECTIONAL DYNAMIC SPINAL FIXATION DEVICE," the entire contents of which are hereby expressly incorporated by reference for all purposes.

BACKGROUND OF THE INVENTION

The present invention relates to a spinal fixation device for spinal fusion and particularly relates to a uni-directional anterior cervical spinal fixation plate device for progressively maintaining a bone graft between adjacent vertebrae under compression.

Spinal plates have been developed for stabilization of the spine upon spinal fusion. Conventional anterior cervical spinal fixation plates typically comprise a unitary plate having a pair of bone screw openings at each of its opposite ends. The plate has sufficient length to span an excavated bone graft-receiving site in the vertebral column and in which site a bone graft is located for fusion to adjacent vertebrae. These prior anterior cervical fixation plates fix the adjacent vertebrae on opposite sides of the bone graft-receiving site relative to one another. It will be appreciated, however, that with both ends of the unitary plate secured by screws to the adjacent vertebrae, advantageous and beneficial compression of the bone graft between the adjacent vertebrae and during the fusion process cannot be obtained. While it has been recognized that compression of a bone graft is desirable over time as the graft fuses to the vertebrae, the nature of these unitary anterior cervical spinal plates fixed at opposite ends to the adjacent vertebrae precludes compression of the bone graft beyond any initial compression during the surgical procedure. Consequently, there has developed a need for a spinal fixation device in which the bone graft can be progressively compressed between adjacent vertebrae over time.

SUMMARY OF THE INVENTION

In accordance with a preferred embodiment of the present invention, there is provided a spinal fixation device, preferably an anterior cervical spinal fixation device which dynamically and uni-directionally maintains compressive forces on the bone graft between adjacent vertebrae over time. To accomplish this, and in a preferred embodiment of the present invention, there is provided a fixation device including first and second discrete plates secured to respective vertebrae on opposite sides of a bone graft-receiving site. Particularly, each plate has two or more openings for cooperation with two or more fasteners, for example, bone screws, to fix the plate to one of the vertebra directly adjacent the bone graft-receiving site. The plates are therefore mounted for movement relative to one another.

More particularly, the first and second plates have interlocking elements cooperable to lock the plates to one another in a plurality of positions for progressively compressing the bone graft between the adjacent vertebrae in response to movement, i.e., advancement of the plates toward one another. Moreover, as the plates progressively move toward one another into each advanced position, the plates are prevented from movement away from one another by the interlocked cooperable elements. Stops cooperable between the plates are also provided to limit the total extent of movement of the plates toward one another beyond a predetermined range of movement. Consequently, desirable and beneficial progressive compression of the bone graft material between the adjacent vertebrae is achieved over time.

Further, the first and second plates preferably have male and female parts, the interlocking elements being formed along the male and female parts. For example, the interlocking elements may take the form of ratchet teeth along opposite sides of the male part and cooperating complementary ratchet teeth along opposite sides of a recess on the female part. With the opposite ends of the first and second plates secured to the adjacent vertebrae, respectively, movement of the patient's head causes relative displacement of the first and second plates toward one another, enabling the ratchet teeth to lock the plates in progressively closer positions relative to one another. The ratchet teeth, of course, prevent movement of the first and second plates away from one another once an interlocked advanced position has been obtained. In this preferred embodiment, the male part may have a central slit enabling its legs to flex laterally toward and away from one another to facilitate progressive engagement of the ratchet teeth between the male and female parts.

In another preferred embodiment of the present invention, the male and female parts may have cooperable, laterally projecting interlocking elements and notches, respectively. The elements are preferably biased, for example, by springs or resilient material, into a lateral outward position for releasable locking in corresponding notches. The elements are free for lateral inward displacement in response to movement of the patient's head to lock in the notches thereby affording a progressive compression of the bone graft between the adjacent vertebrae. It will be appreciated that the locking elements can be provided on one or the other of the male and female parts with the notches lying along the opposite part.

In each embodiment hereof, guides or rails are formed along the plates to prevent misalignment of the plates, i.e., prevent relative movement of the plates in anterior or posterior directions. Preferably, the guides or rails are formed along opposite sides of the male and female parts to maintain the plates aligned with one another.

In a preferred embodiment according to the present invention, there is provided apparatus for compressing a bone graft between adjacent vertebrae, comprising a spinal fixation device including first and second discrete plates having openings for cooperation with fasteners to secure the plates to respective vertebrae on opposite sides of the bone graft, the first and second plates having interlocking elements cooperable to enable progressive advancement of the plates toward one another and to lock the plates to one another in a plurality of advanced positions precluding movement of the plates away from one another for progressively compressing the bone graft between the adjacent vertebrae.

In a further preferred embodiment according to the present invention, there is provided apparatus for compressing a bone graft between adjacent vertebrae, comprising a spinal fixation device including first and second discrete plates, the first and second plates having interlocking elements cooperable, when the plates are secured to the respective vertebrae in an initial position relative to one another, to enable advancement of the plates toward one another and to lock the plates to one another in at least one advanced position precluding movement of the plates away from one another for compressing the bone graft between the adjacent vertebrae.

BRIEF DESCRIPTION OF THE DRAWINGS

FIGS. 7 and 8 are views similar to FIGS. 5 and 6, with the elements located on the female part and notches on the male part; and FIG. 9 is an enlarged cross-sectional view taken about on line 9-9 in FIG. 1 illustrating guides or rails for maintaining the discrete plates aligned with one another.

DETAILED DESCRIPTION

Figure 1:
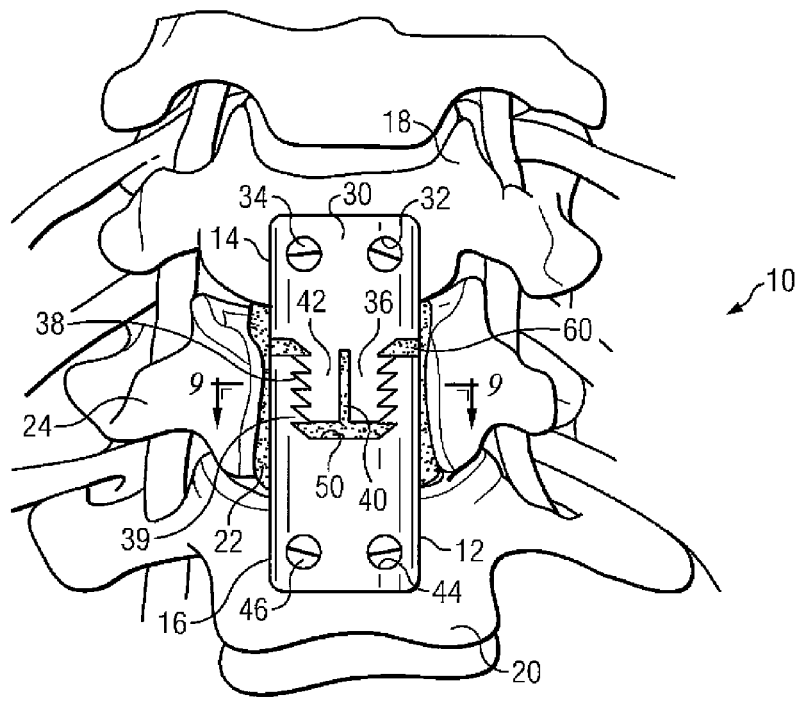
FIG. 1 is an anterior view of a uni-directional dynamic spinal fixation device constructed in accordance with a preferred embodiment of the present invention and illustrated applied to adjacent vertebrae on opposite sides of a bone graft-receiving site.
Figure 2:
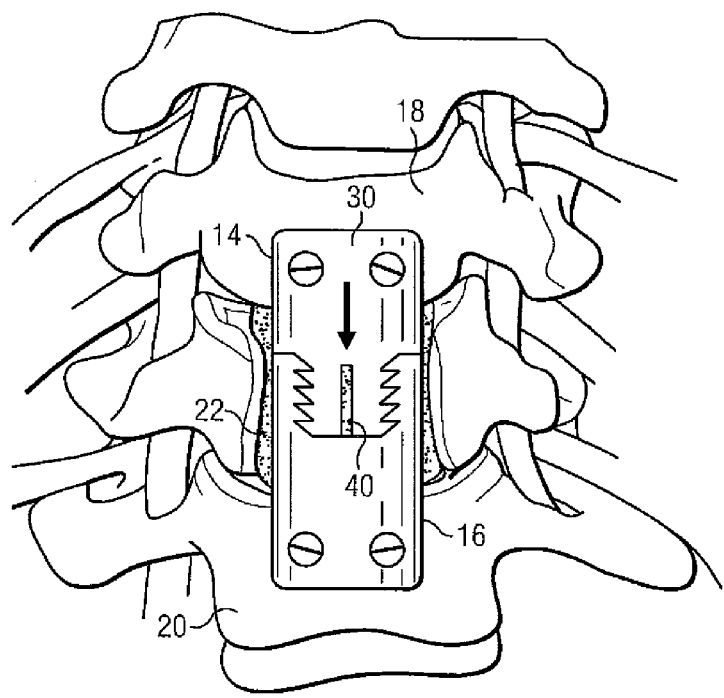
FIG. 2 is a view similar to FIG. 1 illustrating discrete plates of the device in an extreme position precluding further compression of the bone graft material between adjacent vertebrae.

Referring now to the drawings, particularly to FIGS. 1 and 2, there is illustrated a spinal fixation device, generally designated 10, including first and second plates 14 and 16, respectively. As illustrated, the fixation device 10 is disposed in the vertebral column between adjacent vertebrae 18 and 20 which span a bone graft-receiving site 22. The site 22 includes a portion of the intervening vertebra 24 including disks which have been excavated and in which site bone graft material has been disposed. Particularly, an anterior cervical portion of the spinal column is illustrated in FIGS. 1 and 2 with the uni-directional dynamic spinal fixation device of the present invention spanning the graft-receiving site and fixed to the adjacent vertebrae 18 and 20.

The first or superior plate 14 includes a body portion 30 having at least a pair of openings 32 for receiving bone screws 34 whereby the first plate 30 is secured to the vertebra 18 superior to the bone graft site 22. The first plate 30 also includes a male projecting part 36 which projects from an end of the first plate 14 opposite the end containing openings 32 and the bone screws 34. Lateral edges of the male projecting part 36 have elements for interlocking the first and second plates 14 and 16, respectively, to one another, as described below. Preferably, the elements include ratchet teeth 38. Additionally, the male projecting part 36 includes a central slot 40 opening at the distal end of the male part 36 and terminating in a main body portion of the first plate 14. The slot 40 enables the opposite legs 42 of the male part 36 to resiliently flex laterally toward and away from one another, for reasons discussed below.

The second or inferior plate 16 includes a female part defining a recess 50 at an end thereof remote from the openings 44. The recess 50 receives the male part 36 of the first plate 14. The openings 44 receive bone graft screws 46 for securing the second plate 16 to the inferior vertebra 20 on the opposite side 12 of the bone graft-receiving site 22 from vertebra 18. The lateral margins of the recess 50 have interlocking elements, i.e., ratchet teeth 39, which cooperate with and are complementary shaped relative to the ratchet teeth 38 of the male part. Temporarily disposed between the first and second plates 14 and 16 is a spacer 60. The spacer 60 maintains the first and second plates spaced from one another during the course of surgery and serves to aid in proper positioning of the first and second plates relative to one another. It will be appreciated that the male and female parts may be reversed, i.e., the male part 36 may be formed on the inferior plate 16 and the female part 50 may be formed on the superior plate 14.

Once the site 22 has been prepared and the bone graft material 26 (FIG. 3) located in the site between the adjacent vertebrae 18 and 20, the spinal plates 14 and 16 hereof are applied anteriorly of the cervical spinal column. Particularly, using standard surgical techniques, the bone screws 34 are applied through the openings 32 in the ends of the first and second plates into the vertebrae 18 and 20, respectively, to secure the plates to the vertebrae. When securing the plates to the vertebrae, the male part and female parts are interconnected through the interlocking cooperable elements, i.e., the ratchet teeth 38 and 39, in predetermined initial positions, for example, as determined by spacer 60. It will be appreciated that with the spacer 60 located between the first and second plates, the spacer 60 and the interlocked ratchet teeth of the plates prevent movement of the plates toward and away from one another, respectively. When the plates are properly secured to the adjacent vertebrae 18 and 20, the spacer 60 is removed. It will be appreciated that, with the removal of the spacer 60, the plates 14 and 16 are enabled for movement toward one another by the cooperating sloped surfaces of the ratchet teeth 38 and 39. Thus, as the patient recovers and moves his/her head forwardly, the first and second plates may relatively move toward one another and incrementally advance a linear distance corresponding to the pitch of the ratchet teeth. While the drawing FIG. 1 illustrates a range of movement of one tooth pitch, it will be appreciated that additional ratchet teeth are preferably provided to afford a predetermined range of movement of the plates relative to one another.

More particularly, when advanced, the teeth 38 and 39 cooperate with one another to prevent return movement of the plates in a direction away from one another. This dynamic uni-directional movement of the plates toward one another and the locking of the plates in progressively advanced positions responsive to movement of the patient's head anteriorly, thus progressively displaces the adjacent vertebrae 18 and 20 toward one another thereby enabling the bone graft to be maintained under compression between the adjacent vertebrae 18 and 20. Depending upon the distance of travel allowable for the plates relative to one another for each stepwise advance, periodic continued movement of the patient's head in a forward direction, as when nodding, will cause further ratcheting action with consequent advantageous and beneficial compression of the bone graft between the adjacent vertebrae. It will be appreciated that the ratchets have very fine teeth and the movement is incremental, the teeth in the drawing figures being enlarged and exaggerated to demonstrate the concept. It will also be appreciated that the slit 40 separating the legs of the male part permit the legs to flex toward and away from one another, enabling the plates to incrementally advance toward one another.

Referring to FIG. 2, the plates are illustrated in a position in which further advancement of the plates toward one another is prevented. That is, the leading edge of the male part 36 engages the base of the recess 50. Also, the shoulders on the opposed first and second plates engage one another to stop any further relative movement of the plates toward one another. It will be appreciated that other types of stops may be employed. Thus, the range of uni-directional dynamic movement is limited and predetermined.

Figure 3:
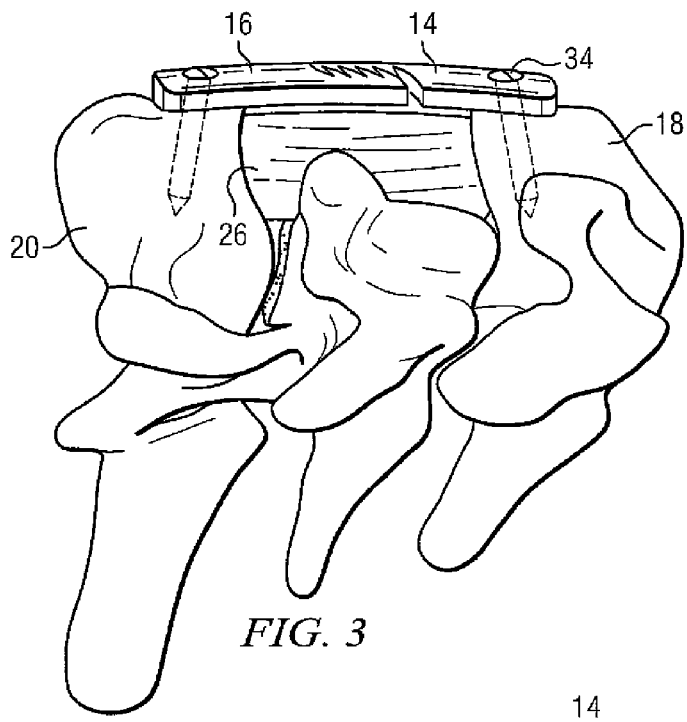
FIGS. 3 and 4 are lateral and end views, respectively, of the spinal plate hereof fixed to the vertebral column.
Figure 4:
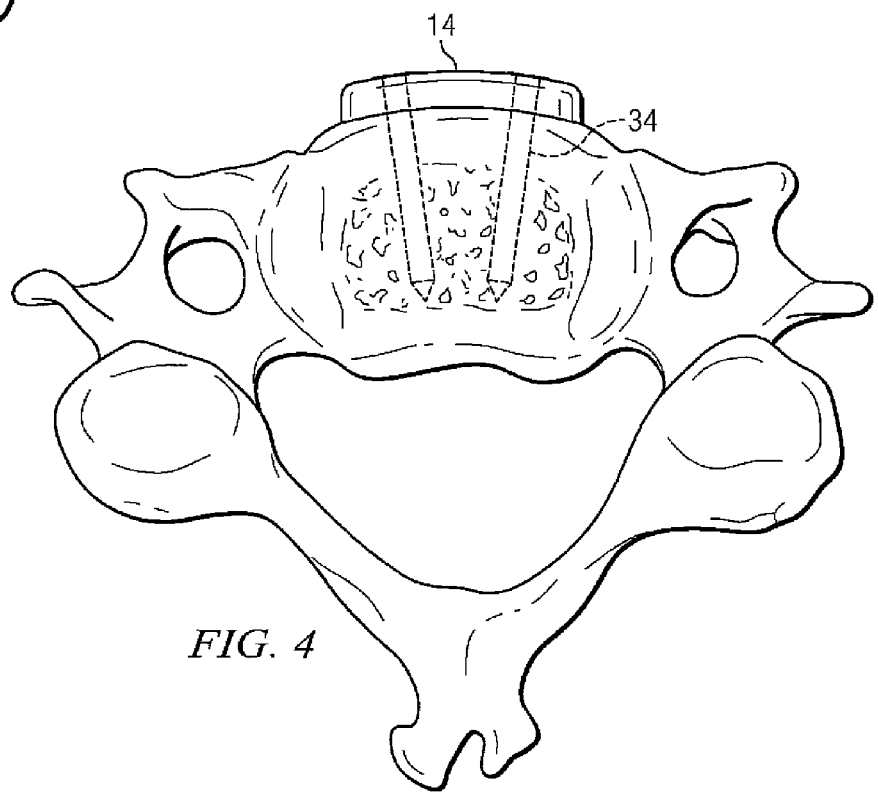

FIGS. 3 and 4 illustrate a preferred embodiment of the uni-directional dynamic spinal fixation device 10 hereof in lateral and endwise views. It will be appreciated that the device is curved, both lengthwise and laterally, with its posterior surface facing the vertebral column being concave in both respects.

Figure 5:
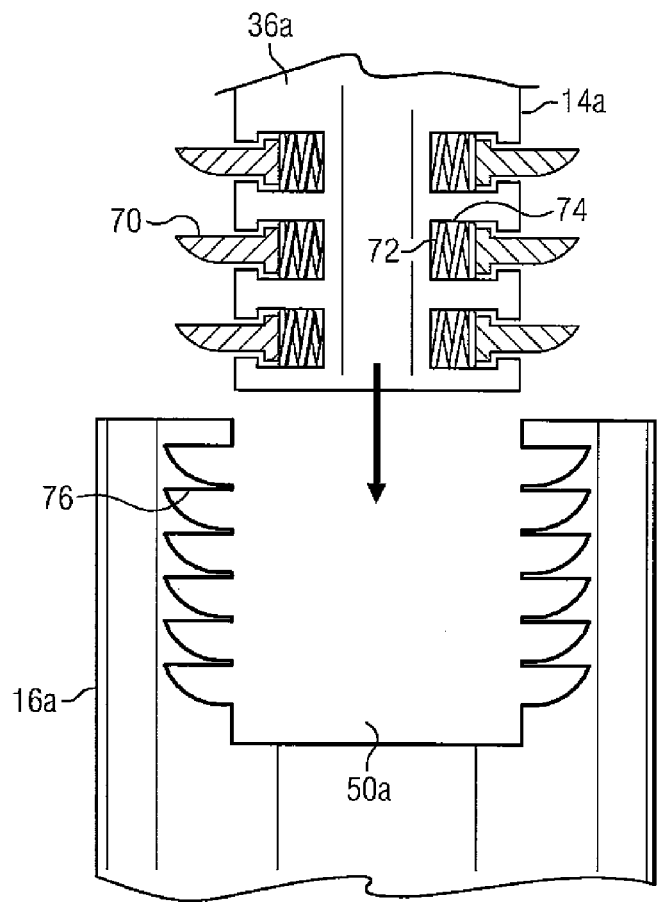
FIGS. 5 and 6 illustrate a further embodiment of the invention with resilient, laterally extending locking elements and lateral notches in the male and female parts of the plate, respectively.
Figure 6:
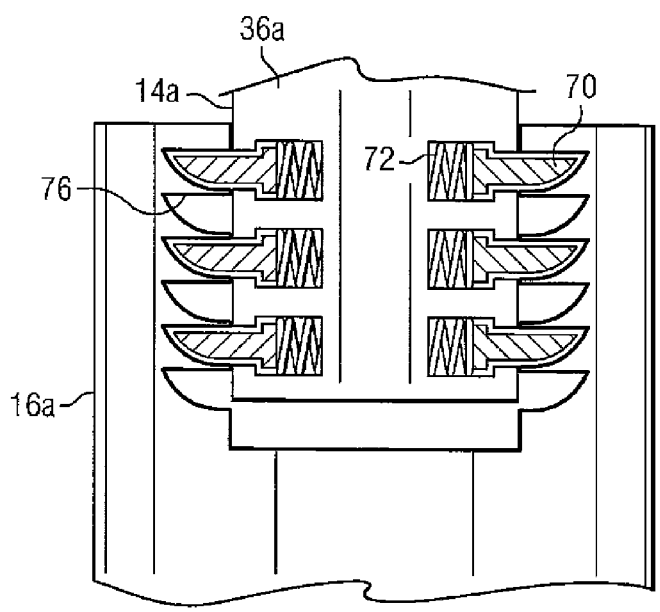

Referring now to the embodiment hereof illustrated in FIGS. 5 and 6, wherein like reference numerals are applied to like parts as in the preceding embodiment, followed by the suffix a, the interlocking elements may comprise a plurality of teeth 70 projecting laterally from the male part 36a of the first plate 14a. The teeth 70 are maintained biased laterally outwardly by springs 72 disposed in recesses 74 in the male part 36a. Thus, it will be seen that a plurality of teeth 70 project laterally outwardly from opposite sides of the male part 36a under the bias of springs 72. Rather than individual springs 72, alternate means to bias the teeth outwardly may be provided. For example, the teeth on each side may be interconnected to one another along a base lying in a channel with a wave spring biasing the base and hence the teeth laterally outwardly. As a further alternative, surgical resilient material may be employed behind each tooth 70 or behind a gang of teeth located in a channel along each side of the male part 36a to provide the lateral outward bias.

The second plate 16a has a plurality of notches 76 along opposite margins of its recess 50a for cooperation with the teeth 70. The teeth 70 and the cooperating notches 76 are configured to enable the first and second plates to move toward one another and to be locked in a plurality of positions locating the first and second parts progressively closer to one another.

FIGS. 7 and 8 illustrate a reverse configuration with respect to the interlocking components shown in FIGS. 5 and 6. That is, the male part 36b of the first plate 14b has a plurality of notches 80 along its opposite margins. The second plate 16b has a plurality of the projections 70b along opposite margins and projecting laterally inwardly into the recess 50b. The projections are biased for lateral movement toward the opposing projection by springs 72b or other biasing means as noted above in connection with springs 72. It will be appreciated that similarly as in the embodiment of FIGS. 5 and 6, as the patient moves his/her head in a direction tending to move the first and second plates toward one another, the projections and notches cooperate to interlock with one another in the progressively advanced positions, preventing the first and second parts from separating movement.

Referring now to FIG. 9, the first and second plates are prevented from moving out of alignment relative to one another in anterior or posterior directions. For example, in the first embodiment hereof illustrated in FIGS. 1-4, the inferior plate 16 may include guides or rails 90 forming channels 92 along the margins of the female recess 50. The teeth 39 of the inferior plate 16 also lie within the channel 92. The teeth 38 on opposite sides of the male part 36 of the superior plate 14 also extend within the channels 92. Consequently, the male and female parts are prevented from displacement in anterior and posterior directions relative to one another. It will be appreciated that the channels may be formed on the margins of the male part with the teeth of the female part projecting into the channels. With respect to the embodiments hereof of FIGS. 5, 6 and 7, 8, similar channels or rails may be provided on one or the other of the male and female parts to prevent misalignment of the parts in forward or rearward directions upon relative movement of the plates toward one another or when in a locked position relative to one another.

It will also be appreciated that the spinal fixation device of the present invention may be formed of materials, such as titanium, compatible for use in the human body over periods of time.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An apparatus for treating a spinal disorder, comprising: a spinal fixation device including first and second plates each having a pair of generally laterally aligned openings for cooperation with fasteners to secure the first and second plates to adjacent vertebrae, the first and second plates each having first and second sets of lateral interlocking elements cooperable with one another to enable progressive postoperative advancement of the plates toward one another and to lock the first and second plates to one another in a plurality of advanced positions precluding movement of the first and second plates away from one another in each the advanced position for progressively compressing a bone graft between the adjacent vertebrae, one of the first and second plates including a leg mounting one of the first and second sets of interlocking elements for flexing movement toward and away from another of the first and second sets of interlocking elements to enable the progressive advancement and locking of the first and second plates to one another.

2. The apparatus of claim 1, wherein the first and second plates are generally coplanar with one another.

3. The apparatus of claim 1, wherein the first and second sets of lateral interlocking elements extend only a portion of the spinal fixation device.

4. The apparatus of claim 1, wherein the leg comprises a plurality of teeth projecting laterally outwardly from the leg on opposite sides of the leg.

5. The apparatus of claim 1, wherein the leg is one of a pair of legs and wherein the pair of legs flexes toward and away from one another in response to movement of the vertebrae toward one another.

6. The apparatus of claim 1, wherein each of the pair of legs comprises a plurality of teeth projecting laterally outwardly on opposite sides of the pair of legs.

7. The apparatus of claim 1, wherein the leg comprises a plurality of notches on opposite sides of the leg.

8. The apparatus of claim 1, wherein the leg comprises a plurality of springs disposed therein.

9. The apparatus of claim 1, wherein the leg projects from an end of the first plate.

10. The apparatus of claim 9, wherein an end of the second plate comprises a recess configured to receive the leg of the first plate.

11. The apparatus of claim 10, wherein one of the first and second sets of interlocking elements is located on lateral margins of the recess.

12. The apparatus of claim 10, wherein the recess comprise a plurality of teeth.

13. The apparatus of claim 10, wherein the recess comprise a plurality of notches.

14. The apparatus of claim 10, wherein the recess comprise a plurality of springs.

15. The apparatus of claim 10, wherein the recess comprise a plurality of channels, guides, or rails along margins of the recess.

* * * * *